US009723854B2

(12) United States Patent
Greiner-Stoeffele et al.

(10) Patent No.: US 9,723,854 B2
(45) Date of Patent: Aug. 8, 2017

(54) HEAT-STABLE ASPARAGINASE FOR REDUCING ACRYLAMIDE IN FOOD STUFFS OR STIMULANTS

(75) Inventors: Thomas Greiner-Stoeffele, Leipzig (DE); Marc Struhalla, Leipzig (DE)

(73) Assignee: C-LECTA GMBH, Leipzig (DE)

( * ) Notice: Subject to any disclaimer, the term of this patent is extended or adjusted under 35 U.S.C. 154(b) by 373 days.

(21) Appl. No.: 12/663,800

(22) PCT Filed: Jun. 12, 2008

(86) PCT No.: PCT/EP2008/004742
§ 371 (c)(1),
(2), (4) Date: Mar. 18, 2010

(87) PCT Pub. No.: WO2008/151807
PCT Pub. Date: Dec. 18, 2008

(65) Prior Publication Data
US 2011/0052758 A1 Mar. 3, 2011

(30) Foreign Application Priority Data

Jun. 13, 2007 (DE) ........................ 10 2007 027 825

(51) Int. Cl.
| A23F 5/16 | (2006.01) |
| A23F 5/00 | (2006.01) |
| C12N 15/63 | (2006.01) |
| C12N 9/78 | (2006.01) |
| A21D 8/04 | (2006.01) |
| A23F 5/02 | (2006.01) |
| A23F 5/22 | (2006.01) |
| A23G 1/02 | (2006.01) |
| C12N 9/82 | (2006.01) |
| A23L 5/20 | (2016.01) |
| A23L 19/18 | (2016.01) |
| A23L 33/17 | (2016.01) |

(52) U.S. Cl.
CPC .............. A23F 5/163 (2013.01); A21D 8/042 (2013.01); A23F 5/02 (2013.01); A23F 5/22 (2013.01); A23G 1/02 (2013.01); A23L 5/25 (2016.08); A23L 19/18 (2016.08); A23L 33/17 (2016.08); C12N 9/82 (2013.01); C12Y 305/01001 (2013.01)

(58) Field of Classification Search
CPC ... A23F 5/163; A23F 5/02; A23F 5/22; A23G 1/02
USPC ................................. 426/45, 629
See application file for complete search history.

(56) References Cited

U.S. PATENT DOCUMENTS

| 3,717,470 A | 2/1973 | Yokotsuka et al. |
| 5,719,056 A | 2/1998 | Brummet et al. |
| 5,756,714 A * | 5/1998 | Antrim et al. ................ 536/102 |
| 6,063,409 A | 5/2000 | Sato et al. |
| 7,037,540 B2 | 5/2006 | Elder et al. |
| 7,396,670 B2 | 7/2008 | Budolfsen et al. |
| 2004/0081724 A1 | 4/2004 | Dria et al. |
| 2006/0275879 A1 | 12/2006 | Lynblev et al. |

FOREIGN PATENT DOCUMENTS

| EP | 1 704 782 | 9/2006 |
| EP | 1 886 582 | 2/2008 |
| JP | 2004 283062 | 3/2003 |
| WO | 2004/032648 | 4/2004 |
| WO | WO2004037007 | * 5/2004 ............... A23F 5/00 |
| WO | 2008 110513 | 9/2006 |
| WO | 2006 128843 | 12/2006 |

OTHER PUBLICATIONS

Friedman, M. 2003. Chemistry, biochemistry and safety of Acrylamide. A reviw. j. Agric. Food Chem. 51:4504-4526.*
Sequence search results—ID Q8TZE8_PYRFU.*
Laderman, K. A. et al. 1993. alpha-amylse from hyperthermophilic Archaebacterium Pyrococcus furiosus. J. Biol. Chem. 268: 24402-24407.*
Witkowski, A. et al. Biochemistry, 38: 11643-11650 (1999).*
Seffernick, J. et al. J. Bacteriol. 183: 2405-2410 (2001).*
Voorhorst, G. B. et al. J. Bacteriol. 1995, 177: 7105-7111.*
Grzybowska, B. et al. Molecular Biotechnology. 2004, 26: 101-109.*
Wang, L. et al. J. Ind. Microbiol. Biotechnol. 2007, 34: 187-192.*
Fischer, B. et al. Biotechnology and Bioengineering. 1993, 41: 3-13.*
Jorgensen, S. et al. J. Biol. Chem. 1997. 272: 16335-16342.*
Robb, F. T. et al. 2001. Methods in Enzymology. 30: 134-157.*
Database EMBL "Pyrococcus furiosu DSM 3638, Section 171 of 173 of the complete genome"; XP002510347.
Genbank, AAL82171, I-asparaginase [Pyrococcus furiosus DSM 3638] Feb. 25, 2003.
EMBL AE009950 Genomic DNA, Translation AAL82171.1, Pyrococcus furious (Strain ATCC 43587, DSM 3638, JCM), Sequence, May 2012.
Maeder, D.L, et al; Pubmed ID 10430560, EMBL id AE009950; Genetics ISSN: 0016-6731; Aug. 1999, vol. 152, Issue 4, p. 1299-1305.
Borek et al; "Sequence analysis of enzymes with asparaginase activity"; Acta Biochimica Polonica, vol. 48 No. 4, 2001; pp. 893-902.
Wagner, et al.; "Diversity of Thermophilic Anaerobes"; Ann. N.Y. Acad. Sci. 1125: 1-43 (2008).
Declerck, et al; "Engineering the thermostability of Bacillus licheniformis alpha-amylase"; Biologia, Bratislava, 57(Suppl. 11): 203-211 (2002).
Borek et al.; "Sequence analysis of enzymes with asparaginase activity"; Acta. Biochem. Polonica, 48(4): 893-902 (2001).
Warth; "Relationship between the heat resistance of spores and he optimum and maximum growth temperatures of *bacillus* species", J. Bacteriol, 1978, pp. 699-705.

(Continued)

Primary Examiner — Hamid R Badr
(74) Attorney, Agent, or Firm — Norris McLaughlin & Marcus, P.A.

(57) ABSTRACT

The invention relates to the use of an amidohydrolase for preparing foodstuffs or stimulants.

18 Claims, 5 Drawing Sheets

(56) References Cited

OTHER PUBLICATIONS

UniProtKB entry, Hyperthermus butylicus, website:uniprot.org/uniprot/A2BLB5 (2016).

* cited by examiner

Acrylamid = acrylamide;  Probe = Sample

HEAT-STABLE ASPARAGINASE FOR REDUCING ACRYLAMIDE IN FOOD STUFFS OR STIMULANTS

This application is a 371 of PCT/EP2008/004742, filed Jun. 12, 2008, which claims foreign priority benefit under 35 U.S.C. §119 of the German Patent Application No. 10 2007 027 825.1 filed Jun. 13, 2007.

The invention relates to the use of an amidohydrolase for preparing a foodstuff or stimulant.

Foodstuffs containing carbohydrates have been consumed by humans throughout the world for centuries. Nowadays, such foodstuffs are obtained in a wide variety of forms, e.g. in the form of crispbreads, rusks, biscuits, pretzels, white toasting bread, breakfast cereals, biscotti, potato crisps, tortilla chips, chips, rice cakes etc.

Acrylamide is often formed during the processing or preparation of foodstuffs containing carbohydrates, in particular during the heating processes, such as occur during baking, roasting, dry roasting, grilling or deep-frying, for example, and thus concentrates in these foodstuffs. A similar phenomenon is also observed during the preparation of stimulants such as the preparation of coffee, for example.

Test results on the acrylamide concentration in foodstuffs were published by the Swedish Authority for Food Safety for the first time in April 2002. In the same year the World Health Organisation (WHO) published a report that, amongst other things, discussed health risks that could arise as a result of a high acrylamide concentration in foodstuffs (FAO/WHO: "*Health Implications of Acrylamide in Food*", Geneva 2002).

Acrylamide is a substance that acts directly on the human genetic code (DNA). Moreover, acrylamide is converted by enzymes in the liver into glycidamide, which is imputed to have a genotoxic effect. Both acrylamide and glycidamide form compounds with amino acids and nucleic bases and can therefore change the structure and function of the DNA and haemoglobin, for example. Acrylamide is classified overall by experts as carcinogenic, damaging to DNA, poisonous, as causing irritation, hypersensitivity and posing a risk to the reproductive system.

The most important source for the formation of acrylamide in foods is the amino acid asparagine, which is common in foods such as potatoes, rice and cereal, but is also present in quite high concentrations in coffee, dried fruits. If the foodstuff/stimulant also contains sugar such as e.g. fructose or glucose besides asparagine, then the formation of acrylamide is promoted even further at high temperatures.

Preparation processes for foodstuffs or stimulants including pretreatment steps for reducing the acrylamide content are already known from the prior art (cf. U.S. Pat. No. 7,037,540, US 2004/81724 or US 2005/202153, for example). Processes in which enzymes, in particular asparaginases, are used for pretreatment are also known from the prior art. These pretreatment steps that are to facilitate the removal, inactivation and/or extraction of asparagine from the foodstuffs or stimulants to be prepared are very costly and/or time-consuming in some instances.

Thus, processes for the preparation of coffee beans respectively include, for example, complex drying, steaming or wetting steps. The purpose of such pretreatment steps is to open the pores of the coffee beans so that the asparagine contained in the coffee beans can be extracted, reduced or inactivated in a better manner.

In a drying operation the coffee beans are heated at temperatures of below approximately 50° C. to then be soaked in asparagine-inactivating solutions such as e.g. calcium lactate or calcium citrate.

In a steaming/wetting operation the coffee beans are sprayed with steam or with water at low pressure or atmospheric pressure, during which the moisture is absorbed by the beans. The beans are then usually treated with asparagine-inactivating solutions in a separate step.

All the abovementioned complex, and in some instances also time-consuming, pretreatment steps directly or indirectly incur elevated costs, since they prolong the whole preparation process and therefore also make it more expensive.

Therefore, the object forming the basis of the invention is to improve the preparation processes for foodstuffs or stimulants known from the prior art. Such improvements should in particular simplify pretreatment steps for the reduction of the asparagine or acrylamide content in foodstuffs or stimulants so that the entire preparation process can be made shorter and less costly.

This object is achieved by the subject of the patent claims.

It has been surprisingly found that foodstuffs or stimulants can be prepared using an amidohydrolase, which after an incubation duration of 5 min at 50° C. has a residual activity of at least 75%.

The invention relates to the use of an amidohydrolase, preferably asparaginase, which after an incubation duration of 5 min at 50° C. has a residual activity of at least 75%, for the preparation of a foodstuff or a stimulant, preferably to reduce the content of asparagine in the foodstuff or stimulant. The reduction of the asparagine content preferably also causes the acrylamide content in the foodstuff or stimulant to be reduced because asparagine is a precursor of acrylamide, when the foodstuff or stimulant is subjected to a subsequent thermal treatment.

Figure 5:
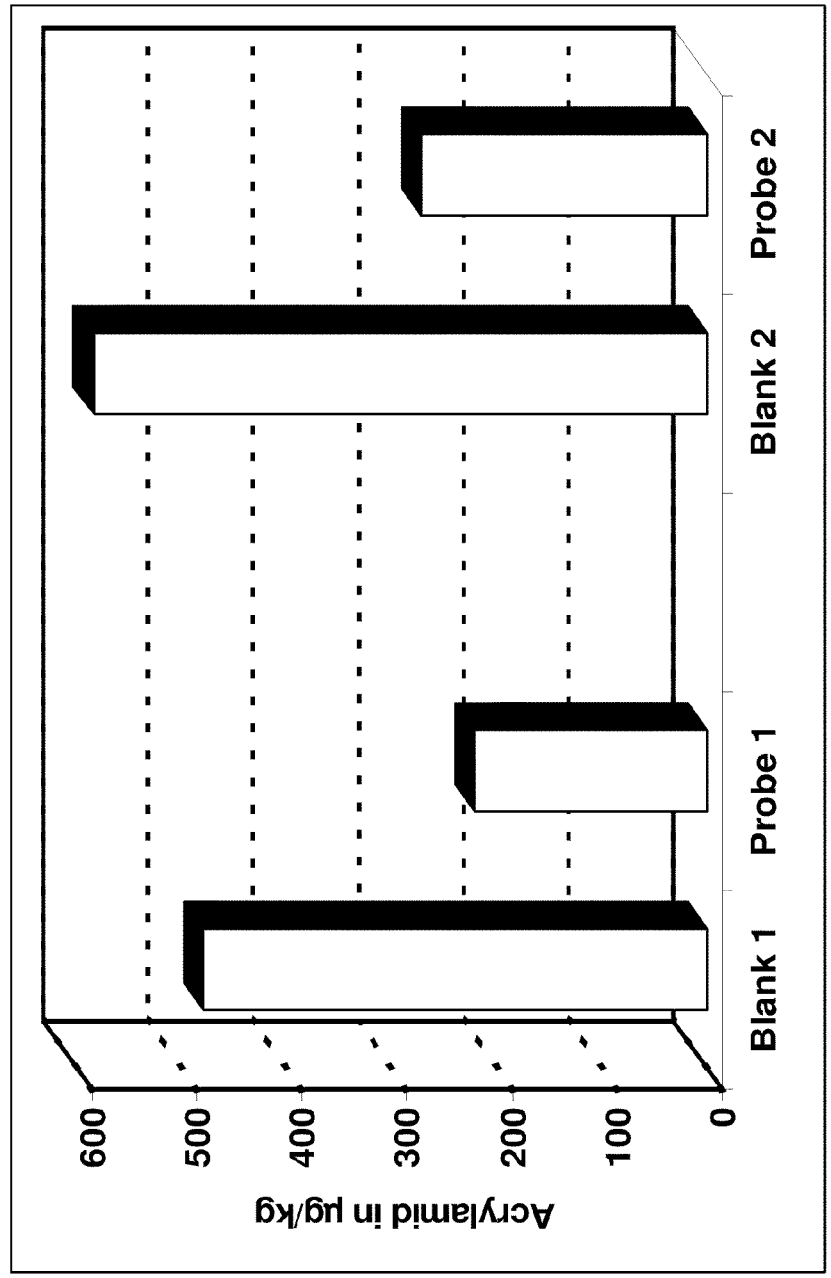

FIG. 5 shows the reduction of the acrylamide content after roasting two types of coffee by pretreating the raw coffee beans with the asparaginase according to the invention as in Example 4 at 80° C. Blank 1 and sample 1—coffee type arabica mixture, blank 2 and sample 2—coffee type Brazil arabica.

Amidohydrolases belong to the enzyme family of hydrolases. The distinguishing feature of amidohydrolases is that they split/hydrolyse amide groups. They are coordinated under EC numbers EC 3.5.1 and 3.5.2 (Enzyme Commission number according to the definition of the *Nomenclature Committee of the International Union of Biochemistry and Molecular Biology*(NC-IUBMB).

In the sense of the description, the term "residual activity" is understood to mean any specific/volumetric enzymatic activity that an enzyme has after a specific incubation duration at a specific temperature compared with the original specific/volumetric activity in the range of its temperature optimum under otherwise identical reaction conditions (pH, substrate etc.). In this case, in the sense of the description the specific/volumetric activity of an enzyme is understood to mean a specific amount of a converted substrate (in μmol) per unit time (in min) per enzyme amount (in mg or ml). The residual activity of an enzyme results from the specific/volumetric activity of the enzyme after the aforementioned incubation duration divided by the original specific/volumetric activity expressed as a percentage (%). In this case, the specific activity of an enzyme is preferably indicated in U/mg and the volumetric activity of an enzyme is preferably indicated in U/ml. Alternatively, the specific/volumetric activity of an enzyme can also be indicated in katal/mg or katal/ml in the sense of the description.

The term "enzymatic activity", sometimes also referred to as "catalytic activity" or "catalytic efficiency", is generally known to the person skilled in the art and refers to the conversion rate of an enzyme and is usually expressed by means of the ratio $k_{kat}/K_M$, wherein $k_{kat}$ is the catalytic constant (also referred to as turnover number) and the $K_M$ value corresponds to the substrate concentration, at which the reaction rate lies at half its maximum value. Alternatively, the enzymatic activity of an enzyme can also be specified by the specific activity (μmol of converted substrate×mg$^{-1}$×min$^{-1}$; cf. above) or the volumetric activity (μmol of converted substrate×ml$^{-1}$×min$^{-1}$; cf. above). Reference can also be made to the general literature such as Voet et al., "Biochemie" [Biochemistry], 1992, VCH-Verlag, Chapter 13, pages 331-332 with respect to enzymatic activity.

In preferred embodiments $A_1$-$A_7$ to $F_1$—$F_7$, the amidohydrolase used according to the invention has a residual activity of preferably at least 75%, more preferred at least 80% and most preferred at least 90%, under the conditions specified in the following table:

| | | Temperature (° C.) | | | | | |
|---|---|---|---|---|---|---|---|
| No. | Duration | A | B | C | D | E | F |
| 1 | 5 min | 50 | 60 | 70 | 80 | 90 | 100 |
| 2 | 10 min | 50 | 60 | 70 | 80 | 90 | 100 |
| 3 | 20 min | 50 | 60 | 70 | 80 | 90 | 100 |
| 4 | 30 min | 50 | 60 | 70 | 80 | 90 | 100 |
| 5 | 40 min | 50 | 60 | 70 | 80 | 90 | 100 |
| 6 | 50 min | 50 | 60 | 70 | 80 | 90 | 100 |
| 7 | 60 min | 50 | 60 | 70 | 80 | 90 | 100 |

In the above table embodiment $C_6$, for example, means that after at least 50 minutes at 70° C. the amidohydrolase has a residual activity of at least 75%, more preferred at least 80%, most preferred at least 90%. In a particularly preferred embodiment, the amidohydrolase has a residual activity in the range of preferably 75-100%, more preferred 75-90%, under the conditions specified above.

In a preferred embodiment, the amidohydrolase used is an asparaginase. In the sense of the description, an asparaginase is understood to be an enzyme that catalyses the hydrolysis of asparagine to aspartate and ammonium. In a preferred embodiment, this is a type I asparaginase and in another preferred embodiment a type II asparaginase.

The amidohydrolase, preferably asparaginase, is preferably thermoactive.

In the sense of the description, "thermoactive" means that the temperature optimum of such amidohydrolases, preferably asparaginases, lies above 50° C.

The term "temperature optimum" is generally known to the skilled person and relates to the temperature range, at which an enzyme exhibits its maximum enzymatic activity. Reference can be made in association with this to the relevant literature such as e.g. Voet et al., "Biochemie", 1992, VCH-Verlag, Chapter 13, page 331; I. H. Segel, Enzyme Kinetics: Behavior and Analysis of Rapid Equilibrium and Steady-State Enzyme Systems, Wiley Interscience, 1993; and A. G. Marangoni, Enzyme Kinetics: A Modern Approach, Wiley Interscience, 2002.

In the sense of the description, the temperature optimum is preferably understood to be the temperature range, in which the amidohydrolase used according to the invention has at least 80%, preferably at least 90% of the maximum enzymatic activity under otherwise constant reaction conditions.

The temperature optimum of the amidohydrolase, preferably asparaginase, preferably lies in the range of 60° to 130° C., more preferred in the range of 70° to 120° C., further preferred in the range of 75° to 110° C., most preferred in the range of 80° to 100° C. and in particular in the range of 85° to 95° C.

The amidohydrolases, preferably asparaginases, used according to the invention are preferably therefore not only heat-stable (i.e. withstand a thermal treatment in respect of their enzymatic activity), but are additionally thermoactive (i.e. only develop their full enzymatic activity at elevated temperature).

No process are known thus far from the prior art in which a thermoactive asparaginase has been used for the treatment of foodstuffs or stimulants to reduce the acrylamide content.

In a preferred embodiment, at a temperature of preferably 60° to 120° C., more preferred 65° to 110° C., further preferred 70° to 100° C., most preferred 75° to 100° C. and in particular 80° to 90° C., the amidohydrolase, preferably asparaginase, has a specific activity of preferably at least 100, more preferred at least 200, further preferred at least 300, further preferred at least 500, most preferred at least 800 and in particular at least 100 units/mg, wherein 1 unit is defined as the amount of amidohydrolase that releases 1.0 μmol of ammonia per minute from L-asparagine at the corresponding reaction temperature and a pH value of 8.6 (50 mM tris-HCl, pH adjustment at 25° C.).

It has been surprisingly found that thermoactive asparaginases have substantial advantages over other asparaginases. For instance, the breakdown of the asparagine can be conducted at comparatively high temperatures using thermoactive asparaginases, and this results in a compatibility with processes in which high temperatures, in particular holding processes at high temperatures, still play a role. Moreover, the breakdown of asparagine at higher temperatures can be conducted at a higher reaction rate.

For example, in the enzymatic treatment of coffee beans it is necessary to allow the green coffee beans to swell in water before they can be treated with enzyme. The coffee beans must then be dried again before they can be roasted. The enzymatic treatment of coffee therefore requires, inter alia, the following steps: a) wetting; b) enzymatic treatment in wetted state; c) drying; d) roasting.

Usual industrial processes for decaffeination or ensuring "mild taste" already include the aforementioned process steps a), c) and d).

For the drying step c) the coffee beans must be heated to a sufficient temperature, since the water cannot otherwise be removed. The heating and wetting of the coffee beans is preferably conducted using hot steam (>100° C.). The subsequent drying step c) is then performed at 70-80° C.

If the amidohydrolase used only had a temperature optimum of 50° C., for example, then this would be very unfavourable, since it would firstly have to be cooled to 50° C. for the enzyme treatment and then heated again for drying.

In contrast, no cooling is necessary when using the thermoactive asparaginases preferred according to the invention and this represents a particular advantage of the invention.

A further advantage when using thermoactive asparaginases is that the diffusion of the asparagine to be hydrolysed is increased as a result of the elevated temperature, and this likewise results in an improved efficiency of the process according to the invention.

The process according to the invention enables a preparation operation to be obtained using an amidohydrolase while retaining the process steps of usual processes for the preparation of a foodstuff or a stimulant, i.e. without any serious changes to the process cycles. The enzymatic treatment can preferably be conducted during a process step, in which the foodstuff or stimulant is nevertheless exposed to an elevated temperature.

In a further preferred embodiment, at a temperature of preferably 60° to 120° C., more preferred 65° to 110° C., further preferred 70° to 100° C., most preferred 75° to 100° C. and in particular 80-90° C., the amidohydrolase, preferably asparaginase, has a volumetric activity of preferably at least 50, more preferred at least 100, further preferred at least 300, further preferred at least 500, most preferred at least 800 and in particular at least 1000 units/mg, wherein 1 unit is defined as the amount of amidohydrolase that releases 1.0 μmol of ammonia per minute from L-asparagine at the corresponding reaction temperature and a pH value of 8.6 (50 mM tris-HCl, pH adjustment at 25° C.).

In a preferred embodiment, the amidohydrolase, preferably asparaginase, has a pH optimum in the range of preferably pH 1 to pH 14, more preferred in the range of pH 3 to pH 12, further preferred in the range of pH 5 to pH 11, most preferred in the range of pH 7 to pH 10 and in particular in the range of pH 8 to pH 9. The term "pH optimum" is generally known to the skilled person and relates to the pH range, in which an enzyme has its maximum enzymatic activity. Reference can be made in association with this to the relevant literature such as e.g. Voet et al., "Biochemie", 1992, VCH-Verlag, Chapter 13, page 331. In the sense of the description, the term pH optimum is preferably understood to mean the pH range, in which the amidohydrolase used according to the invention has at least 80%, preferably at least 90% of the maximum enzymatic activity under otherwise constant reaction conditions.

It has been surprisingly found that amidohydrolases, preferably asparaginases, that are active over a very broad pH range can be provided. In the range from pH 5-pH 10, these amidohydrolases, preferably asparaginases, preferably have an activity of at least 10% of the maximum activity. As a result of this, it is possible to use this enzyme in different processes with widely differing pH ranges. It is also possible to use it in processes in which the pH value is subject to significant fluctuations in the process. Processes are also possible in which pH values from 5 to 10 occur. In the treatment of green coffee beans using tap water, for example, very low pH values of ~5 can occur.

In a preferred embodiment, over the entire pH range of 5-10, the amidohydrolase, preferably asparaginase, according to the invention has an activity of at least 10%, more preferred at least 15%, further preferred at least 20%, most preferred at least 25% and in particular at least 30% compared to the maximum activity, i.e. to the maximum activity with the optimum pH value under otherwise identical conditions, preferably at optimum temperature and concentration.

The amidohydrolase, preferably asparaginase, used according to the invention is preferably stable in storage. In preferred embodiments $G_1$-$G_{17}$ to $K_1$-$K_{17}$, the amidohydrolase has a residual activity of at least 80%, more preferred at least 85% further preferred at least 90% and in particular at least 95%, under the conditions specified in the following table:

|   | Storage Period | Temperature Range (° C.) | | | | |
|---|---|---|---|---|---|---|
|   |   | G | H | I | J | K |
| 1 | 5 days | 25 | 15 | 10 | 8 | 5 |
| 2 | 10 days | 25 | 15 | 10 | 8 | 5 |
| 3 | 15 days | 25 | 15 | 10 | 8 | 5 |
| 4 | 20 days | 25 | 15 | 10 | 8 | 5 |
| 5 | 25 days | 25 | 15 | 10 | 8 | 5 |
| 6 | 30 days | 25 | 15 | 10 | 8 | 5 |
| 7 | 60 days | 25 | 15 | 10 | 8 | 5 |
| 8 | 90 days | 25 | 15 | 10 | 8 | 5 |
| 9 | 120 days | 25 | 15 | 10 | 8 | 5 |
| 10 | 150 days | 25 | 15 | 10 | 8 | 5 |
| 11 | 180 days | 25 | 15 | 10 | 8 | 5 |
| 12 | 210 days | 25 | 15 | 10 | 8 | 5 |
| 13 | 240 days | 25 | 15 | 10 | 8 | 5 |
| 14 | 270 days | 25 | 15 | 10 | 8 | 5 |
| 15 | 300 days | 25 | 15 | 10 | 8 | 5 |
| 16 | 330 days | 25 | 15 | 10 | 8 | 5 |
| 17 | 360 days | 25 | 15 | 10 | 8 | 5 |

In the above table, embodiment $I_5$, for example, means that after storage for 25 days at 10° C., the amidohydrolase has a residual activity of at least 80%, more preferred at least 85% further preferred at least 90% and in particular at least 95%. In a particularly preferred embodiment, in the case of storage at 4° C. over a period of 30 days, the amidohydrolase used according to the invention has a residual activity of at least 80%.

The amidohydrolase group comprises, inter alia, the enzyme family of the asparaginases (EC 3.5.1.1), which catalyse the hydrolysis of asparagine to aspartate and ammonia. In a preferred embodiment, the amidohydrolase used according to the invention is an asparaginase.

It is generally known that asparaginases can convert both asparagine (L and D form) and glutamine (L and D form).

In view of this substrate promiscuity of asparaginases, the asparaginase used according to the invention hydrolyses L-asparagine preferably more quickly than L-glutamine and/or possibly more quickly than D-asparagine.

The ratio of the $K_M$ values (respectively in mM) of L-asparagine to L-glutamine preferably lies in the range of 1:10 to 1:400, more preferred in the range of 1:20 to 1:200, further preferred in the range of 1:30 to 1:100, most preferred in the range of 1:40 to 1:80.

In a preferred embodiment, the asparaginase used according to the invention prefers L-asparagine to L-glutamine and/or to D-asparagine. The ratio of the $K_M$ values (respectively in mM) of L-asparagine to L-glutamine preferably lies in the range of 1:1 to 1:400, more preferred in the range of 1:5 to 1:100, further preferred in the range of 1:10 to 1:50.

Amidohydrolases or asparaginases can be heat-labile or heat-stable. Heat-stable asparaginases are already known from the prior art (cf. e.g. Li et al., Anal. Chem. 2002, 74, pp 3336-3341, U.S. Pat. No. 5,719,056 or Agathi et al., Mol. Cell. Biochem. 2001, 216, pp 93-101). However, indications for their use in processes for preparing foodstuffs or stimulants are not evident from these publications.

In the sense of the description, the terms "heat-stable amidohydrolase" or "heat-stable asparaginase" are preferably to be understood to mean an amidohydrolase or asparaginase, which after an incubation duration of 5 mM at 50° C. has a residual activity of at least 75%.

The asparaginase is preferably an asparaginase selected from *Archeoglobus* sp. (e.g. *Archeoglobus fulgidus*), *Therms* sp. (e.g. *Thermus therophilus*), *Pyrococcus* sp. (e.g. *Pyrococcus abyssi*), *Thermococcus* sp. (e.g. *Thermococcus kodakarensis*), *Methanothermobacter* sp. (e.g. *Methanothermobacter thermautrophicus*) or an asparaginase selected from further Euryarchaeota or asparaginase I from *Pyrococcus furiosus*.

In a preferred embodiment, the asparaginase is coded by a nucleotide sequence, which preferably has at least 60%, more preferred at least 80%, further preferred at least 90%, further preferred at least 95%, most preferred at least 99% and in particular at least 99.9% homology with the nucleotide sequence <SEQ ID NO: 1>. In this case, the homology is preferably determined by means of the algorithm according to Smith & Waterman (J. Mol. Biol., 1981, 147(1), 195-7) using the BLOSUM62 matrix and values of 11.0 for the opening of a gap or 1.0 for expanding a gap.

It is preferred in particular that the asparaginase used according to the invention is coded by the nucleotide sequence <SEQ ID NO: 1>.

In a preferred embodiment, the amino acid sequence of the asparaginase has at least 50%, more preferred at least 75%, further preferred at least 80%, further preferred at least 90%, further preferred at least 95%, most preferred at least 99% and in particular at least 99.9% homology (sequence identity) with the amino acid sequence <SEQ ID NO: 2>. In this case, the homology is preferably determined by means of the algorithm according to Smith & Waterman (J. Mol. Biol., 1981, 147(1), 195-7) using the BLOSUM62 matrix and values of 11.0 for the opening of a gap or 1.0 for expanding a gap.

In another particularly preferred embodiment, the asparaginase used according to the invention comprises the amino acid sequence <SEQ ID NO: 2>.

As already stated above, preparation processes for foodstuffs or stimulants preferably containing carbohydrates frequently have pretreatment steps to reduce the acrylamide content in these foodstuffs or stimulants. It is therefore preferred that the use of the amidohydrolase according to the invention serves in the preparation, in particular as part of a pretreatment operation, to hydrolyse asparagine to asparaginic acid.

In the sense of the description, the term "foodstuff containing carbohydrates" is preferably understood to mean foodstuffs having a carbohydrate content amounting to preferably at least 0.1% by wt., more preferred at least 1% by wt., further preferred at least 5% by wt., further preferred at least 10% by wt., most preferred at least 20% by wt. and in particular at least 30% by wt. in relation to the total weight of the foodstuff.

It is additionally preferred that the use of an amidohydrolase according to the invention serves in the preparation, in particular as part of a pretreatment operation, to reduce the content of asparagine and/or acrylamide in the foodstuff or stimulant.

As a result of such a use of an amidohydrolase according to the invention, a reduction in the content of asparagine preferably occurs so that the foodstuff or stimulant has a reduced content of acrylamide during a thermal aftertreatment.

In the sense of the description, the term "thermal aftertreatment" is preferably understood to mean the processes that are accompanied by a heating of the foodstuff or stimulant. Usual thermal aftertreatments comprise heating, dry roasting, grilling, boiling, cooking, baking, steaming, deep frying and the like.

It is particularly preferred if the amidohydrolase used according to the invention is suitable for use in preparation processes for foodstuffs containing carbohydrates such as, for example, rice, bread and baked goods, snack foods, ready mixes, dried fruits, animal feed etc. or stimulants such as coffee or cocoa. Such foodstuffs and/or stimulants are preferably selected from the group comprising crispbread, rusks, biscuits, pretzels, white toasting bread, waffles, muffins, bagels?, croissants, brownies, breakfast cereals, biscotti, potato crisps, tortilla chips, corn chips, crackers, nuts, chips, rice cakes, polenta, couscous, pancakes, ready-mixes, cake mixes, biscuit mixes, bread mixes, croutons, dog food, cat food, coffee beans, cocoa beans.

Coffee beans are particularly preferred. Preferred coffee bean types are *Coffea arabica*, *Coffea canephora*, *Coffea liberica* and *Coffea robusta*.

In a particularly preferred embodiment, the preparation of a stimulant comprises a decaffeination and/or washing of coffee beans, in which the amidohydrolase according to the invention is used.

In a likewise particularly preferred embodiment, the preparation of a stimulant comprises a hydrolysis of coffee beans combined with the use of the amidohydrolase, preferably asparaginase, according to the invention. Coffee beans are subjected to a steam treatment during the course of the preparation of a decaffeination process or for taste enhancement. In this case, the beans are heated intensely and brought into contact with water. The use of a thermoactive amidohydrolase has proved to be particularly advantageous here for reducing the asparagine concentration in the green coffee bean. The enzyme use at temperatures over 70° C. allows complete compatibility with established processes and in addition allows very high reaction rates, which greatly reduce the process times.

The use of an amidohydrolase, preferably asparaginase, according to the invention having the above-described properties results in numerous surprising advantages, which are outlined below on the basis of four illustrative examples. A skilled person knows that such examples should not be considered to be in any way restrictive, since the amidohydrolase according to the invention is suitable for use in a plurality of preparation processes for foodstuffs or stimulants.

Thus, in the preparation of potato crisps, the potatoes are usually pretreated with asparaginase before they are cooked in steam, i.e. the potatoes are cut into slices and the asparaginase can either be sprayed onto them or the potato slices are dipped into a solution containing asparaginase. The duration of such a conventional asparaginase treatment can be substantial in some instances (up to several hours), since because of the temperature optimum of the enzyme (usually 37° C., cf. e.g. U.S. Pat. No. 7,037,540, Example 5)

the treatment temperature must amount to 37° C. at maximum and the breakdown of asparagine is correspondingly slow.

As a result of the heat-stable properties of the amidohydrolase used according to the invention, the potato slices are subjected to an asparaginase treatment at higher temperatures, i.e. the asparagine reduction occurs more quickly, inter alia because the solubility of asparagine increases at higher temperatures. In some instances, by virtue of the heat-stable properties of the enzyme, the asparaginase treatment can even occur simultaneously while the potatoes are being cooked in steam. In this case, the asparaginase can be sprayed onto the potato slices beforehand, for example.

A deactivation of the amidohydrolase is conducted in a conventional manner by means of a thermal aftertreatment, i.e. by deep-frying the potato slices. Therefore, there are no health concerns with respect to the use of these heat-stable amidohydrolases.

A further example relates to the decaffeination of coffee beans. In this preparation process, the unroasted green coffee beans are subjected to steam treatment and/or are soaked in partially hot water in order to extract the caffeine from the beans. By means of the amidohydrolase used according to the invention it is possible to combine such decaffeination steps, which usually operate at temperatures above 37° C., with a simultaneous asparaginase treatment, i.e. the preparation process for decaffeinated coffee as such is less time-consuming and therefore less expensive. Conventional processes for the decaffeination of coffee beans are known to the skilled person and include, amongst others, the "Swiss water process", the "direct method", the "indirect method" or the "triglyceride process". Reference can be made to R. Heiss, Lebensmitteltechnologie: Biotechnologische, chemische, mechanische and thermische Verfahren der Lebensmittelverarbeitung [Food technology: biotechnological, chemical, mechanical and thermal processes for food processing], Springer, 6th edition, 2003, for example, in its entirety in this context.

Surprisingly, the amidohydrolase according to the invention can also be used particularly advantageously in a steaming/wetting treatment for coffee beans. As already stated above, such a steaming/wetting treatment serves to open the pores of the coffee beans so that the asparagine present in the beans can be subsequently inactivated/reduced more easily. A steaming/wetting treatment usually occurs at elevated temperatures, i.e. at temperatures preferably up to 100° C. at maximum, since the solubility of asparagine is increased in warm solvent and also the pores of the coffee beans open more quickly at warm temperatures. With the aid of the heat-stable amidohydrolase according to the invention a reduction of asparagine can occur simultaneously during the steaming/wetting treatment and at the same time the asparagine reduction can run more quickly and efficiently because of the high temperature tolerance of the enzyme.

The amidohydrolase according to the invention can also be used in the production of fresh baked goods such as bread, bread rolls or the like. These fresh baked goods are often produced using cooking/extrusion processes, which usually operate at temperatures between 95° and 105° C. Because of the heat-stable properties of the amidohydrolase according to the invention the enzyme can be added during cooking/extrusion and thus effect a reduction of the asparagine content. What is important for asparagine reduction in the case of cooking extrusion is the kneading of the dough as well as the formation of gas bubbles that form as carbon dioxide escapes from the heated water. The amidohydrolase according to the invention is inactivated or denatured as a result of the subsequent baking or roasting process, which usually operates in the temperature range of 200° to 600° C.

Many steps for the treatment of foodstuffs and stimulants involve incubation operations in aqueous medium at high temperatures between 70° and 110° C., and these precede the thermal aftertreatment that leads to the formation of acrylamide. These include cooking steps, for example. Water treatments in the above temperature range are used, for example, in the production of shaped chips or shaped potato crisps. The unexpected advantage of the asparaginase according to the invention is that the enzyme can be used directly in these processes and achieves very high reaction rates at the high temperatures, thus enabling very high activity rates with very small enzyme quantities.

The amidohydrolase can also be advantageously used in cereal processing processes. In the production of corn flakes corn grits are cooked in mixture with sugar, salt and malt and then further processed and roasted. The roasting causes the unwanted formation of acrylamide. During cooking temperatures between 70° and 100° C. are reached that are very well suited to using the amidohydrolase according to the invention to enable the formation of acrylamide to be suppressed.

Extrusion processes are very often involved in cereal processing. For example, extrusion processes are conducted at an end temperature of 80-100° C. in the production of breakfast cereals. Processes are also described which include holding processes at high temperatures between 70° and 100° C.

Products that are processed at high temperatures and contain rye generally have very high acrylamide contents (for example, crispbread). High temperatures are reached very quickly in the baking process for the production of crispbread. The crispbread can be treated with a solution of the amidohydrolase according to the invention prior to the baking process in order to reduce the acrylamide formation during the baking process.

A further unexpected advantage of the heat-stable amidohydrolase used according to the invention is the possibility of reusing (recycling) the enzyme. Thus, the amidohydrolase that is not denatured even at elevated temperatures, i.e. up to preferably 100° C., because of its heat-stable properties can be extracted after use or separated using another method and thus used for a new application. Such a recycled amidohydrolase solution can go through many, i.e. preferably at last 1, 2, 3, 4 or 5, cycles for the reduction of asparagine.

The application of the amidohydrolases used according to the invention is preferably deemed safe with respect to health, since these amidohydrolases are natural non-toxic substances.

A further aspect of the present invention relates to a process for preparing a foodstuff or a stimulant comprising the steps:

(i) incubating the foodstuff or stimulant with an amidohydrolase as defined above at an incubation temperature of preferably at least 50° C., more preferred at least 60° C., further preferred at least 70° C., further preferred at least 80° C., most preferred at least 90° C. and in particular at least 99° C.; and;

(iii) if necessary, heating the foodstuff or stimulant to a temperature lying preferably at least 10° C., more preferred at least 15° C., further preferred at least 20° C., most preferred at least 50° C. and in particular at least 60° C. above the incubation temperature.

In a preferred embodiment, the process for preparing a foodstuff or a stimulant according to the invention comprises the steps:
(i) incubating the foodstuff or stimulant with an amidohydrolase as defined above at an incubation temperature of preferably at least 50° C., more preferred at least 60° C., further preferred at least 70° C., further preferred at least 80° C., most preferred at least 90° C. and in particular at least 99° C.;
(ii) separating the amidohydrolase from the foodstuff or stimulant or inactivating the amidohydrolase;
(iii) if necessary, heating the foodstuff or stimulant to a temperature lying preferably at least 10° C., more preferred at least 15° C., further preferred at least 20° C., most preferred at least 50° C. and in particular at least 60° C. above the incubation temperature; and
(iv) if necessary, reusing the amidohydrolase separated in step (ii) in step (i).

Step (i) of the process according to the invention is preferably conducted under conditions (time, temperature, pH value, quantity of amidohydrolase etc.) such that the amount of (free) asparagine originally contained in the foodstuff or stimulant is reduced by at least 50%, more preferred at least 75%, further preferred at least 80%, further preferred at least 85%, most preferred at least 90% and in particular at least 95%. A person skilled in the art can determine suitable conditions through usual routine testing.

Step (ii) of the process according to the invention is preferably conducted under conditions (time, temperature, pH value, quantity of amidohydrolase etc.) such that the amount of acrylamide formed in the possibly subsequent thermal aftertreatment is reduced by at least 20%, preferably 30%, further preferred by at least 40% and most preferred by at least 50%.

In a preferred embodiment, step (i) of the process according to the invention is preferably conducted under conditions (time, temperature, pH value, quantity of amidohydrolase etc.) such that after conducting step (iii) the amount of acrylamide contained in the foodstuff or stimulant amounts to 200 ppm at most, more preferred 150 ppm at most, further preferred 135 ppm at most, most preferred 100 ppm at most and in particular 50 ppm at most. A person skilled in the art can determine suitable conditions through usual routine testing.

In a likewise preferred embodiment, step (i) of the process according to the invention is preferably conducted under conditions (time, temperature, pH value, quantity of amidohydrolase etc.) such that after conducting step (iii) the amount of acrylamide contained in the foodstuff or stimulant amounts to 1000 µg/kg at most, more preferred 500 µg/kg at most, further preferred 300 µg/kg at most, most preferred 150 µg/kg at most and in particular 50 µg/kg at most. A person skilled in the art can determine suitable conditions through usual routine testing.

In a preferred embodiment step (i) is conducted for at least 240 min, more preferred at least 120 min, further preferred at least 60 min, most preferred at least 20 min and in particular at least 5 min.

In a preferred embodiment, the weight ratio of foodstuff or stimulant to amidohydrolase lies in the range of $10^2$:1 to $10^{10}$:1, more preferred $10^2$:1 to $10^8$:1, further preferred $10^4$:1 to $10^8$:1, most preferred $10^4$:1 to $10^7$:1 and in particular $10^5$:1 to $10^7$:1.

In a preferred embodiment, the amidohydrolase is prepared in an aqueous solution and combined with the foodstuff or stimulant, e.g. by spraying. In this case, the concentration of amidohydrolase in the aqueous solution preferably amounts to $10^{-6}$ to 100 g/l, more preferred $10^{-5}$ to 10 g/l, further preferred $10^{-4}$ to 1 g/l, most preferred $10^{-3}$ to $10^{-1}$ g/l and in particular $10^{-2}$ to $5 \times 10^{-2}$ g/l.

A further aspect of the invention relates to a foodstuff or stimulant that is obtainable by the above-described process. The foodstuff or stimulant preferably has a residual content of 200 ppm at most, more preferred 150 ppm at most, further preferred 135 ppm at most, most preferred 100 ppm at most and in particular 50 ppm at most, of asparagine and/or acrylamide.

A further aspect of the invention relates to a foodstuff or stimulant that is obtainable by the above-described process. The foodstuff or stimulant preferably has a residual content of 400 µg/kg at most, more preferred 300 µg/kg at most, further preferred 200 µg/kg at most, most preferred 100 µg/kg at most and in particular 50 µg/kg at most, of asparagine and/or acrylamide.

A further aspect of the invention relates to a vector which contains a nucleotide sequence as defined above. Such a vector is preferably selected from the group comprising plasmids, cosmids, phagemids, phage-vectors, bacterial artificial chromosomes and yeast artificial chromosomes.

A further aspect of the invention is a process for the production of an amidohydrolase as defined above comprising the following steps:
a) incorporating a vector as defined above into an expression system;
b) if necessary, expressing the amidohydrolase in the expression system;
c) if necessary, digesting or lysing or separating the expression system;
d) if necessary, adding a suitable, possibly heat-stable, nuclease to hydrolyse the nucleic acid of the expression system;
e) if necessary, denaturing the expression system by means of an incubation process at preferably 60° C., more preferred 70° C., further preferred 80° C., most preferred 90° C. and in particular 100° C., for the period of preferably 1 min, more preferred 5 min, further preferred 10 min, most preferred 20 min and in particular 60 min;
f) if necessary, separating unwanted components of the expression system by centrifuging, filtration, microfiltration or ultrafiltration;
g) if necessary, binding the amidohydrolase to a solid support, wherein the binding occurs by ionic, hydrophobic interactions or interactions determined by affinity tag;
h) if necessary, washing the support to remove unwanted components under conditions, in which the amidohydrolase remains substantially bonded to the support;
i) if necessary, eluting the amidohydrolase from the support by suitable buffer conditions;
j) .
k) if necessary, concentrating the amidohydrolase solution by precipitation, ultrafiltration, freeze-drying or drying; and
l) if necessary, transferring the amidohydrolase into a suitable storage buffer.

Natural asparaginases can be localised in an intracellular and extracellular arrangement. If the asparaginases are to be overexpressed in large amounts in an intracellular arrangement, then it is necessary to overcome the problem that high asparaginase concentrations exert a toxic effect in the cell since they hydrolyse the amino acid asparagine that is essential for the cell. It has been surprisingly found that the amidohydrolase according to the invention only has a very low residual activity in the temperature range from 20-37° C., in which the fermentation processes of mesophilic organisms such as e.g. *Escherichia coli, Pseudomonas* sp., *Bacillus* sp., *Pichia pastoris, Saccharomyces cerevisiae* or *Aspergillus* sp. are usually conducted. Thus, at 25° C. the enzyme has a residual activity of <2%. This allows the intracellular expression of the asparaginase according to the invention in mesophilic expression hosts in large numbers.

A further aspect of the invention comprises a process for the production of an amidohydrolase as defined above, in which the amidohydrolase is expressed intracellularly in a microorganism, wherein at the cultivation temperature during the expression of the amidohydrolase the residual activity of the enzyme is <30%, preferably <15%, further preferred <10%, further preferred <5%, most preferred <2%.

Fermentation protocols for microorganisms accessible to the skilled person allow yields of bio wet mass of preferably >100 g/l, more preferred >125 g/l, further preferred >150 g/l, further preferred >175 g/l and most preferred >200 g/l.

In a preferred embodiment, in the case of the intracellular expression of the amidohydrolase in a microorganism, an activity yield of >10 kU/g bio wet mass, more preferred >20 kU/g of bio wet mass, more preferred >40 kU/g bio wet mass, more preferred >60 kU/g bio wet mass, most preferred >80 kU/g bio wet mass, is reached.

In a preferred embodiment, in the case of the intracellular expression of the amidohydrolase in a microorganism, an activity yield of >100 000 units per liter of culture medium, more preferred >500 000 units per liter, more preferred >1 million units per liter, more preferred >3 million units per liter, more preferred >6 million units per liter and most preferred >10 million units per liter, is reached.

In a preferred embodiment the [amidohydrolase] according to the invention is expressed intracellularly in a mesophilic expression host such as e.g. *Escherichia coli, Pseudomonas* sp., *Bacillus* sp., *Pichia pastoris, Saccharomyces cerevisiae* or *Aspergillus* sp.

The following examples serve to explain the invention in more detail, but are not to be interpreted as restrictive.

EXAMPLES

Example 1—Expression of a Heat-Stable Asparaginase

The gene coding for asparaginase I from *Pyrococcus furiosus* (<SEQ ID NO: 1>) was amplified with the two primers PF_AsnI_S (5'-ACCTGCGGTCTCGCAT-GAAAATTCTTC-TAATTGGGATGGG-3'; <SEQ ID NO: 3>) and PF_AsnI_A (5'-GGATCCCTGCAGTT-AATCTCTAAGCTCTCCAACTAG-3'; <SEQ ID NO: 4>) (both Thermo Electron, Ulm) by means of a PCR from *Pyrococcus furiosus* DSM 3638-DNA under the following conditions:
1.1 PCR Conditions:
PCR batch:

| | |
|---|---|
| 10 µl | 10x VENT buffer (NEB, Beverly, USA) |
| 2 µl | dNTPs (each 10 mM) |
| 100 pmol | Primer PF_AsnI_S <SEQ ID NO: 3> |
| 100 pmol | Primer PF_AsnI_A <SEQ ID NO: 4> |
| 1 µl | DNA from *Pyrococcus furiosus* DSM 3638 |
| 2 U | VENT polymerase (NEB) |
| ad 100 µl | dist. H$_2$O |

Temperature profile of PCR:

| | | |
|---|---|---|
| | 2 min/94° C. | |
| 1. | 45 sec/94° C. (denaturing) | |
| 2. | 45 sec/57° C. (attachment) | } 25 x |
| 3. | 60 sec/72° C. (elongation) | |
| | 2 min/72° C. | |

The resulting PCR product was purified using the QIAquick PCR cleaning kit (Qiagen, Hilden) following the manufacturers' instructions.
1.2 Restriction Digestion:

The gene obtained under point 1.1 was cloned in the expression vector pRSF-1b <SEQ ID NO: 5> (Vector pRSF-1 b, Novagen-Merck-Biosciences, Bad Soden).

For this, the PCR product was digested using restriction endonucleases Eco31I and PstI and vector pRSF-1b <SEQ ID NO: 5> using restriction endonucleases NcoI and PstI (all Fermentas, Vilnius, Litauen) as outlined below:
1.3 Restriction Digestion Batches:

| PCR Product | Vector |
|---|---|
| 2 µg PCR product | 4 µg pRSF-1b <SEQ ID NO: 5> |
| 3 µl 10x buffer G$^+$ (Fermentas) | 4 µl 10x buffer Y$^+$ (Fermentas) |
| 10 U Eco31I | 10 U NcoI |
| 20 U PstI | 20 U PstI |
| ad 30 µl dist. H$_2$O | ad 40 µl dist. H$_2$O |

The restriction digestion batches were incubated for 2 hours at 37° C. 1 U SAP (Shrimp Alkaline Phosphatase, Fermentas, Vilnius, Lithuania) was then added to the "vector batch" for dephosphorylation and incubated for a further 30 min at 37° C. The enzymes were then inactivated for 20 min at 80° C. The products were then purified using the QIAquick PCR cleaning kit (Qiagen, Hilden).
1.4 Ligation, Transformation into *E. coli* and Plasmid Reisolation The vector DNA and the PCR product (cf. point 1.3) were joined together by incubation with T4 DNA ligase as outlined below:
Ligase batch:

| | |
|---|---|
| 200 fmol | pRSF-1b <SEQ ID NO: 5> |
| 600 fmol | PCR product |
| 3 µl | 10x ligase buffer (Fermentas) |
| 1 µl | T4 DNA ligase |
| ad 30 µl | dist. H$_2$O |

The batches were incubated for 8 h at 16° C. and the enzyme was then inactivated by incubation for 10 minutes at 65° C. 1 µl of this batch was used directly to transform commercially available competent XL1 Blue Cells (Stratagene, La Jolla, USA) by means of electroporation. The electroporated cells were plated on solid agar plates with kanamycin and cultivated overnight at 37° C. Working from a resulting single colony the finished plasmid was reisolated using the plasmid cleaning kit QIAprep mini-preparation kit (Qiagen, Hilden) following the manufacturers' instructions and the expression plasmid pRSF_Pf-AsnI <SEQ ID NO: 6> was obtained The expression plasmid pRSF_Pf-AsnI <SEQ ID NO: 6> was incorporated into cells by means of electroporation in Rosetta 2 (DE3) (Novagen-Merck-Biosciences, Bad Soden) and the cells were plated onto LB agar plates (10 g trypton, 5 g yeast extract, 10 g NaCl, ad 1 l dist. water) with kanamycin (Kan) and chloramphenicol (Cam).

Single clones were picked from these plates and preliminary cultures were firstly produced for the expression. For this, 100 ml LB (Kan, Cam) medium was inoculated with 1% (w/v) glucose with 1 ml of a 5 ml preculture and shaken at 37° C. and 200 rpm (revolutions per minute) until an $OD_{600}$ of 0.6 was obtained. The cells were centrifuged off (4° C., 15 mM, 3200×g) and the supernatant discarded. The pellet was re-suspended in 2 ml 10% (v/v) of glycerol. The suspension was aliquoted to 200 nl in each case, frozen in liquid nitrogen and stored at −80° C.

The main culture for the expression consisted of 500 ml LB (Kan, Cam) medium with 1% (w/v) glucose. It was inoculated with an aliquot of the preculture. The main culture was incubated at 37° C. and 200 rpm. After an $OD_{600}$ von 0.9 was obtained it was induced with 1 mM IPTG (isopropyl-β-D-thiogalactopyranoside) and shaken overnight at 30° C. and 200 rpm. On the next day the cells were sedimented by centrifuging (4° C., 15 mM, 3200×g) and after removal of the medium the pellet was weighed and re-suspended with 20 ml of lysis buffer (10 mM tris/HCl pH 8.0, 0.5 mg/ml lysozyme) and broken down with ultrasound (5×30 s, 80% power). The suspension of the broken down cells was centrifuged (4° C., 30 mM, 14000×g). The supernatant then underwent incubation for 30 mM at 80° C. and was subjected to renewed centrifuging (4° C., 30 mM, 14000×g). The pellet was discarded and the raw extract thus obtained was removed and stored at 4° C. for further studies. The activity yield was determined at 160 kU from the supernatant (cf. Example 2). A yield of 40 kU per g of bio wet mass was determined from the weight of the cell pellet of 4 g.

Example 2—Determination of the Temperature Profile

Assay Principle

Asparaginases catalyse the conversion of asparagine to aspartate with the release of ammonium ions. These can be indicated using colour reagents such as e.g. Nessler reagent. Alternatively, ammonium ions can also be detected by means of the Berthelot reaction (DIN 38 406 E5). The assay using Nessler reagent is based on an end point determination. In this case, the reaction is incubated over a period of 30 mM at the corresponding temperature, stopped and the ammonium ions formed detected.

Reagents and Solutions
Reagents:
L-asparagine monohydrate: Applichem A3669, MW 150.14 g/mol
Ammonium sulphate: Merck, 1.101211, MW 132.14 g/mol
Nessler reagent: Fluka, 72190
Tris, TCA
Stock Solutions and Buffers:
50 mM Tris/HCl pH 8.6
172 mM L-asparagine solution
1.5 M TCA (trichloroacetic acid)
Calibrating Solutions:
5 mM $(NH_4)_2SO_4$ solution 2.1 Preparation of a Calibration Curve
The following batches were made for this:

| 50 μl in each case | | | | | | 50 mM tris/HCl pH 8.6 |
|---|---|---|---|---|---|---|
| 0 μl | 5 μl | 10 μl | 20 μl | 30 μl | 40 μl | 5 mM $(NH_4)_2SO_4$ |
| 45 μl | 40 μl | 35 μl | 25 μl | 15 μl | 5 μl | dist. $H_2O$ |

The batches were mixed, 5 μl of M TCA were added in each case and the mixture mixed once again.

For each value 860 μl of dist. $H_2O$ were provided in a 1.5 ml reaction vessel and 40 μl of the respective batch added and then mixed. 100 μl of Nessler reagent were added to each batch in one action and the samples were mixed for a short time. After 5 mM the photometer was balanced against water at 436 nm and the samples measured in one action. The values were recorded in a calibration line (cf. FIG. 1).

2.2 Sample Measurement

Using a commercial protein detection test (Bradfort, Bio-Rad Laboratories GmbH, Munich), the protein concentration of the raw extract from exemplary embodiment 1 was determined at approx. 4 mg/ml. The asparaginase solution was diluted 1:2000 in 50 mM tris/HCl pH 8.6. The following batch was presented for each sample to be measured:

| 50 μl | 50 mM tris/HCl pH 8.6 |
|---|---|
| 35 μl | dist. $H_2O$ |
| 5 μl | 172 mM L-Asn solution |

The batches were mixed and a thermocycler was preheated to the desired temperature (37, 70, 80, 90 and 99° C.).

5 μl of the diluted enzyme sample were added to the batches and 5 μl of buffer were added for the blank reading, the batches were mixed for a short time and then incubated for 30 min at the respective reaction temperature. The reactions were then cooled on ice and stopped by adding 5 μl of 1.5 M TCA solution.

The released ammonium ions were then immediately determined. For each value 860 μl of dist. $H_2O$ were provided in a 1.5 ml reaction vessel and 40 μl of the respective batch added and then mixed. 100 μl of Nessler reagent were added to each batch in one action and the samples were mixed for a short time. After 5 min the photometer was balanced against water at 436 nm and the samples measured in one action.

Figure 1:
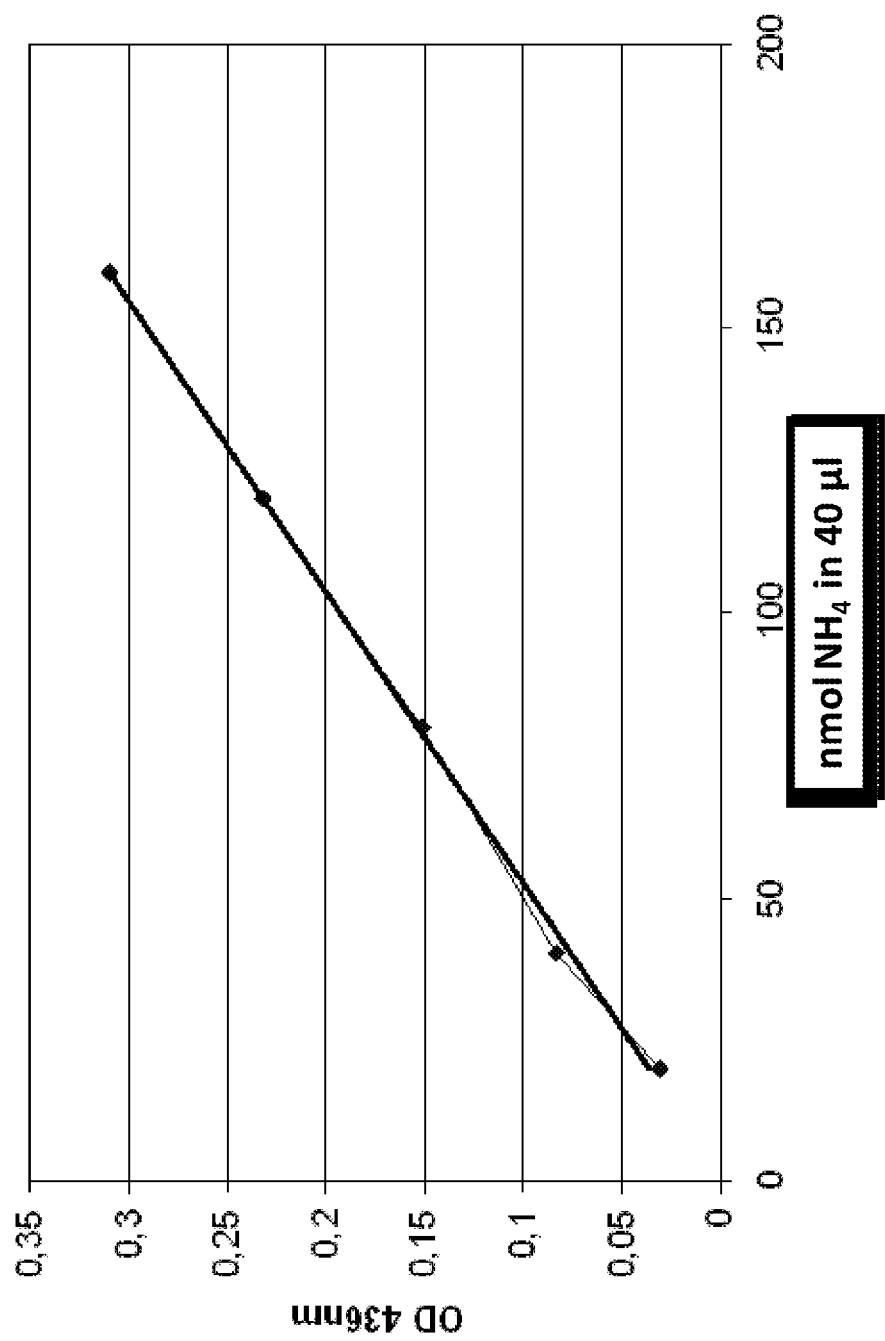
FIG. 1 shows the calibration line of the ammonium ion determination using Nessler reagent. x-axis: amount of $NH_4$ per 40 µl, y-axis: optical density (OD) at 436 nm. The correlation coefficient $R^2$ amounts to 0.9979.

The determined absorption value was firstly converted into released ammonium ions on the basis of the calibration curve (cf. FIG. 1). The volumetric activity [U/min] of the enzyme was then calculated via the definition of the unit (one unit of asparaginase releases 1 μmol of $NH_4$ per mM under assay conditions). Such calculations are generally known to the person skilled in the art.

2.3 Determination of the Temperature Optimum

Figure 2:
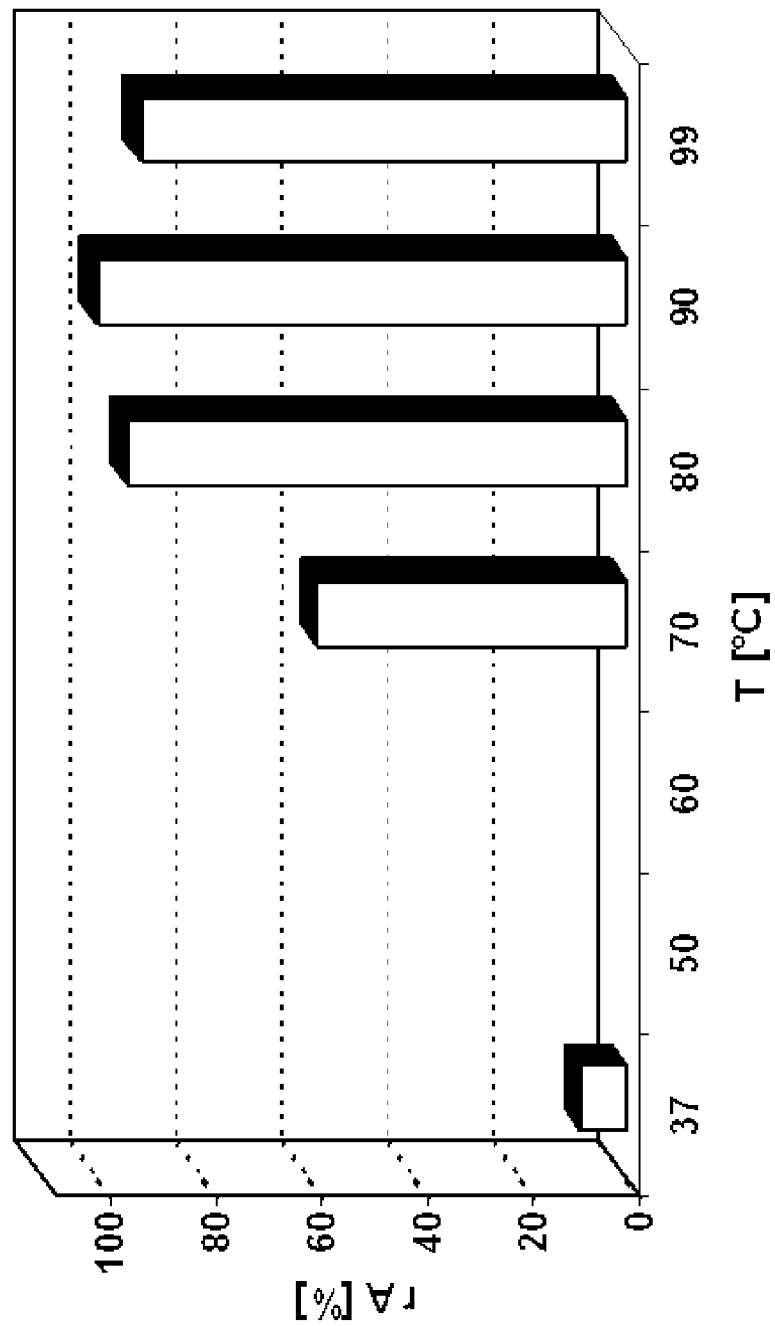
FIG. 2 shows the enzymatic activity of asparaginase I of *Pyrococcus furiosus* at different incubation temperatures. rA: relative activity (in %), T [° C.]: temperature in degrees Celsius.

The content of $NH_4$ was measured at a wavelength of 436 nm for the different temperatures and the resulting volumetric (enzyme) activities determined. The volumetric activity at 90° C. was set at 100% (=reference value) and the respective volumetric activities at the other temperatures were related to this reference value accordingly (=relative activity). The corresponding values are collated in the following table and shown graphically in FIG. 2:

| Temp. | Measured Value 436 nm | Units per ml | Relative Activity |
|---|---|---|---|
| 37° C. | 0.018 | 320 | 9% |
| 70° C. | 0.126 | 2140 | 58% |
| 80° C. | 0.205 | 3460 | 94% |
| 90° C. | 0.218 | 3670 | 100% |
| 99° C. | 0.2 | 3370 | 92% |

Example 3—Determination of the Temperature Stability

Reagents and solutions, the determination of the calibration curve as well as implementation of the activity tests were as described above in exemplary embodiment 2.

3.1 Temperature Stability at 95° C.

Figure 3:
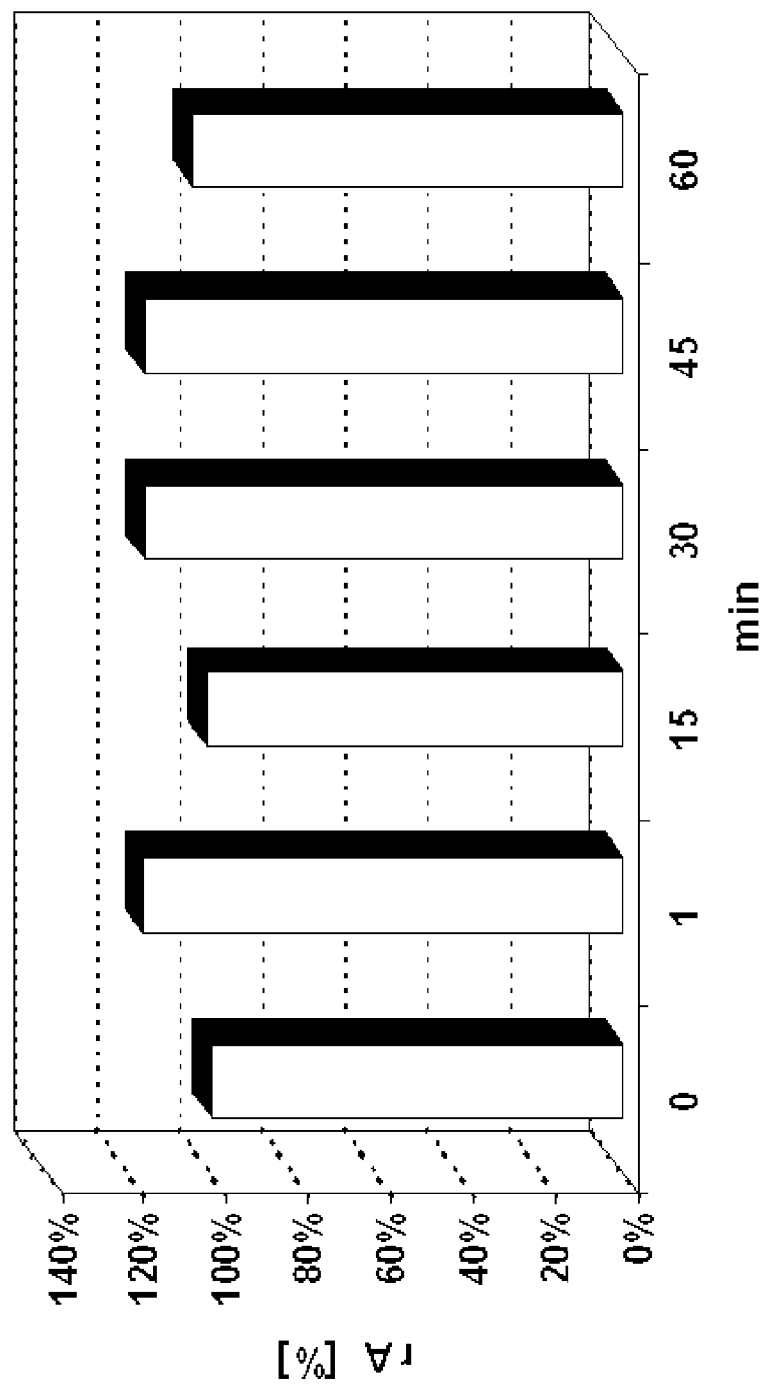
FIG. 3 shows the temperature stability of asparaginase I of *Pyrococcus furiosus* at a temperature of 95° C. rA: relative activity (in %), min: time in minutes. It is evident from the graph that at 95° C. after an incubation duration of 60 minutes the asparaginase has a relative activity or residual activity of approx. 100%.

The determination of the volumetric (enzyme) activity was always conducted at an incubation temperature of 90° C. in this case. For determination of the temperature stability the asparaginase solution from exemplary embodiment 1 was diluted 1:10 in 50 mM tris/HCl pH 8.6 and then pre-incubated at 95° C. for different periods of time (0, 1, 15, 30, 45 and 60 mM) A further dilution of 1:100 was then conducted in 50 mM tris/HCl pH 8.6 and the remaining residual activity determined. The volumetric enzymatic activity without pre-incubation at 95° C. was set at 100% (=reference value) and all other values were related to this reference value (=relative activity). The values thus obtained/calculated are collated in the following table (cf. also FIG. 3):

| Time in min | Measured Value at 436 nm | Units per ml | Relative Activity |
|---|---|---|---|
| 0 | 0.398 | 3340 | 100% |
| 1 | 0.466 | 3900 | 117%* |
| 15 | 0.403 | 3380 | 101%* |
| 30 | 0.464 | 3890 | 116%* |
| 45 | 0.464 | 3890 | 116%* |
| 60 | 0.418 | 3500 | 105%* |

*relative activity = residual activity

3.2 Temperature Stability at 99° C.

Figure 4:
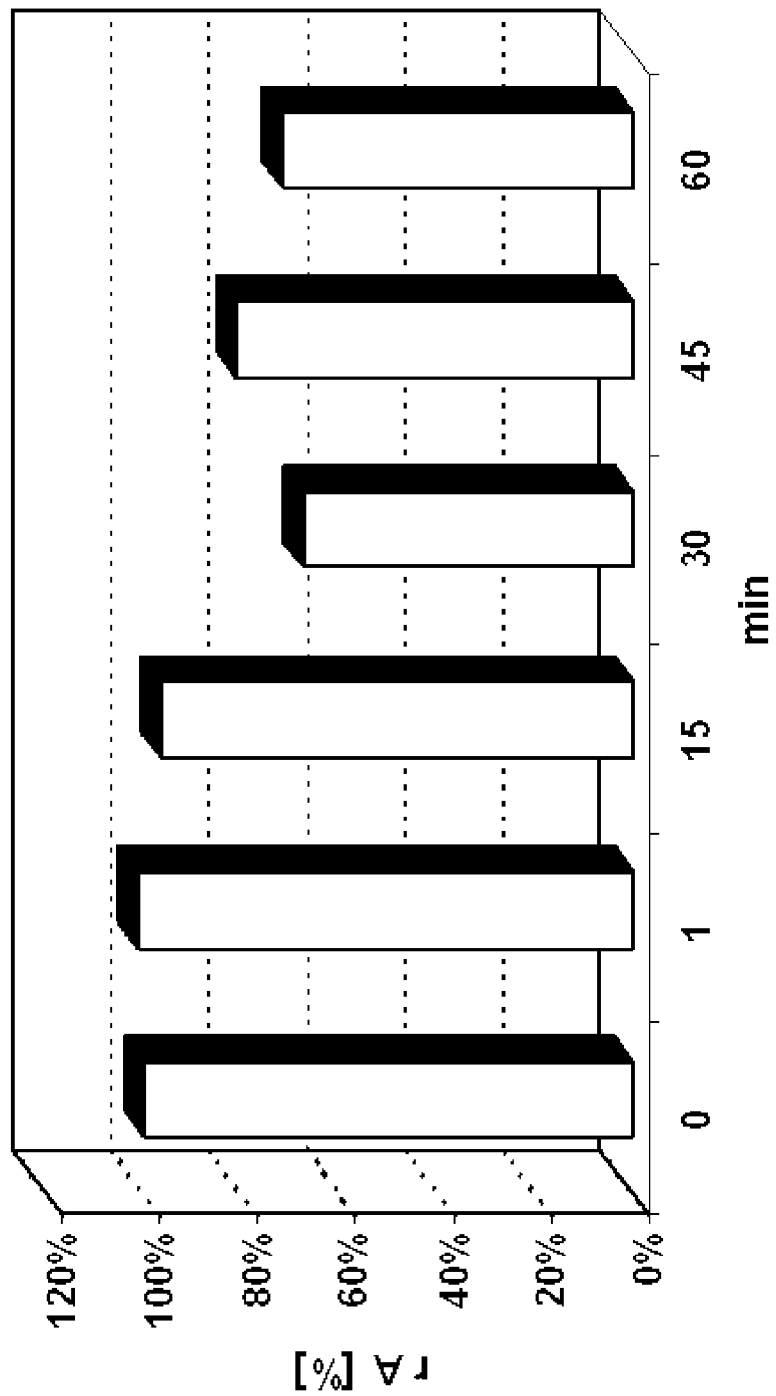
FIG. 4 shows the temperature stability of asparaginase I of *Pyrococcus furiosus* at a temperature of 99° C. rA: relative activity (in %), min: time in minutes. It is evident from the graph that at 99° C. after an incubation duration of 60 minutes the asparaginase has a relative activity or residual activity of approx. 70%.

The test to determine the temperature stability at 99° C. was conducted in the same manner as the test described above in point 3.1. The values thus obtained/calculated are collated in the following table (cf. also FIG. 4):

| Time in min | Measured Value at 436 nm | Units per ml | Relative Activity |
|---|---|---|---|
| 0 | 0.411 | 3440 | 100% |
| 1 | 0.416 | 3490 | 101%* |
| 15 | 0.396 | 3320 | 97%* |
| 30 | 0.276 | 2320 | 67%* |
| 45 | 0.329 | 2790 | 81%* |
| 60 | 0.294 | 2470 | 72%* |

*relative activity = residual activity

Example 4—Reduction of the Acrylamide Content in Coffee Beans

To determine the efficiency of the treatment of foodstuffs with the asparaginase according to the invention raw coffee beans were subjected to a treatment step with the enzyme at 80° C. before roasting and the reduction of the acrylamide content was determined after roasting.

The following test batches were prepared for this:
Blank 1: 500 g raw coffee beans type arabica mixture+267 g 100 mM tris/HCl pH 8.6 (25° C.)
Blank 2: 500 g raw coffee beans type Brazil arabica+267 g 100 mM tris/HCl pH 8.6 (25° C.)
Sample 1: 500 g raw coffee beans type arabica mixture+267 g 100 mM tris/HCl pH 8.6 (25° C.)+1400 units of asparaginase from exemplary embodiment 1
Sample 2: 500 g raw coffee beans type Brazil arabica+267 g 100 mM tris/HCl pH 8.6 (25° C.)+1400 units of asparaginase from exemplary embodiment 1

The blanks and samples were incubated for 60 mM at 80° C. with rotation. The liquid was then filtered off from the coffee beans, the beans dried and roasted.

The acrylamide content was determined by an independently accredited test laboratory. The results of the studies are shown in the following table (cf. also FIG. 4):

| | Acrylamide Content in µg/kg | Average Deviation in µg/kg | Residual Content |
|---|---|---|---|
| Blank 1 | 480 | 20 | 100% |
| Sample 1 | 222 | 19 | 46% |
| Blank 2 | 585 | 35 | 100% |
| Sample 2 | 273 | 18 | 47% |

---

The invention claimed is:

1. A method of preparing a foodstuff or a stimulant, said method comprising: treating the foodstuff, stimulant or a precursor thereof with an amidohydrolase, the amidohydrolase having an amino acid sequence having at least 90% identity to the amino acid sequence of SEQ ID NO: 2, and the amidohydrolase after an incubation duration of 5 min at 50° C. having a residual activity of at least 75%.

2. The method according to claim 1, wherein the amidohydrolase has a temperature optimum in the range of 70° to 120° C.

3. The method according to claim 1, wherein the amidohydrolase has a specific activity of at least 200 units/mg at a temperature in the range of 60° to 120° C.

4. The method according to claim 1, wherein the amidohydrolase has a pH optimum of pH 1 to pH 14.

5. The method according to claim 1, wherein the amidohydrolase after storage at 4° C. over a period of 1 month has a residual activity of at least 80%.

6. The method according to claim 1, wherein over the pH range of pH 5-pH 10 the amidohydrolase has an activity of at least 10% compared to its maximum activity.

7. The method according to claim 1, wherein the amidohydrolase is an asparaginase.

8. The method according to claim 7, wherein the asparaginase is "asparaginase I" from *Pyrococcus furiosus*.

9. The method according to claim 7, wherein the asparaginase is coded by a nucleotide sequence, which has at least 90% identity to the nucleotide sequence SEQ ID NO: 1.

10. The method according to claim 7, wherein the asparaginase is coded by the nucleotide sequence SEQ ID NO: 1.

11. The method according to claim 7, wherein the asparaginase comprises the amino acid sequence SEQ ID NO: 2.

12. The method according to claim 1, wherein preparing said foodstuff or said stimulant serves to hydrolyse asparagine to asparaginic acid.

13. The method according to claim 1, wherein preparing said foodstuff or said stimulant serves to reduce a content of asparagine and/or acrylamide in the foodstuff or stimulant.

14. The method according to claim 13, wherein the reduction in the content of asparagine occurs so that the foodstuff or stimulant has a reduced content of acrylamide during a thermal aftertreatment.

15. The method according to claim 1, wherein the foodstuff or stimulant is selected from the group consisting of crispbread, rusks, biscuits, pretzels, white toasting bread, waffles, muffins, bagels, croissants, brownies, breakfast cereals, biscotti, potato crisps, tortilla chips, corn chips, crackers, chips, rice cakes, polenta, couscous, pancakes, nuts, ready-mixed cake mixes, biscuit mixes, bread mixes, croutons, dog food, cat food, coffee beans and cocoa beans.

16. The method according to claim 15, wherein said preparing comprises decaffenating, washing or decaffenating and washing of coffee beans.

17. A process for preparing a foodstuff or a stimulant comprising the steps:
  (i) incubating the foodstuff or stimulant with an amidohydrolase at an incubation temperature of at least 50° C., the amidohydrolase having an amino acid sequence having at least 90% identity to the amino acid sequence of SEQ ID NO: 2, the amidohydrolase after an incubation duration of 5 min at 50° C. having a residual activity of at least 75%; and
  (ii) optionally, heating the foodstuff or stimulant to a temperature lying at least 10° C. above the incubation temperature.

18. The process according to claim 17, which further comprises the steps:
  (iii) separating the amidohydrolase from the foodstuff or stimulant or inactivating the amidohydrolase; and
  (iv) optionally, reusing the amidohydrolase separated in step (iii) in step (ii).

* * * * *

SEQUENCE LISTING

<160> NUMBER OF SEQ ID NOS: 6

<210> SEQ ID NO 1
<211> LENGTH: 981
<212> TYPE: DNA
<213> ORGANISM: Pyrococcus furiosus

<400> SEQUENCE: 1

```
gtgaaaattc ttctaattgg gatgggtgga acaattgcga gtgtaaaggg cgagaatgga     60
tatgaggctt cgttgtccgt taaagaagtt ttagatatcg ccggaatcaa agattgtgag    120
gattgtgatt ttctcgattt aaagaacgtt gatagcacgc ttatccagcc agaagattgg    180
gtagatcttg ctgaaactct ttacaagaat gtaaaaaaat atgatggaat tatagtcact    240
catggtaccg atactcttgc ctacacttct tcaatgataa gtttcatgct tagaaacccc    300 ccaatacccca tcgtatttac tggttctatg atacctgcca ctgaagaaaa tagtgatgcc    360
```

```
cccctaaact tgcaaacagc aataaagttt gcaacttctg gaattagggg agtttacgtg    420
gccttcaatg gaaaagttat gcttggagtt agaacatcta aggttaggac aatgagcaga    480
gatgcattcg aaagcattaa ctaccctata attgcagaat taagaggaga agatctcgtg    540
gttaacttta ttccaaagtt taacaatgga gaagtcacat tagaccttag cacgatcca    600 aaagttctag ttataaagct aatcccagga ctttcggggg acatatttag ggcagctgta    660
gagctgggat atagaggaat tgtcatagaa ggttatggag ctggaggaat tccttatagg    720
ggaagtgatt tacttcaaac aatagaggag ctctccaagg agattccaat agtaatgaca    780
acccaggcaa tgtacgatgg agttgatcta acgaggtaca aagttgggag attagccctt    840
agagctggag taatcccagc gggggacatg acaaaagagg caacagtaac aaagctcatg    900
tggattctag ccacacaaa caatgtggaa gaaataaaag tattaatgag aaaaaatcta    960
gttggagagc ttagagatta a                                             981
```

<210> SEQ ID NO 2
<211> LENGTH: 326
<212> TYPE: PRT
<213> ORGANISM: Pyrococcus furiosus

<400> SEQUENCE: 2

```
Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
                20                  25                  30

Ile Ala Gly Ile Lys Asp Cys Glu Asp Cys Asp Phe Leu Asp Leu Lys
            35                  40                  45

Asn Val Asp Ser Thr Leu Ile Gln Pro Glu Asp Trp Val Asp Leu Ala
        50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
                85                  90                  95

Leu Arg Asn Pro Pro Ile Pro Ile Val Phe Thr Gly Ser Met Ile Pro
                100                 105                 110

Ala Thr Glu Glu Asn Ser Asp Ala Pro Leu Asn Leu Gln Thr Ala Ile
            115                 120                 125

Lys Phe Ala Thr Ser Gly Ile Arg Gly Val Tyr Val Ala Phe Asn Gly
        130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val
            180                 185                 190

Thr Leu Asp Leu Arg His Asp Pro Lys Val Leu Val Ile Lys Leu Ile
        195                 200                 205

Pro Gly Leu Ser Gly Asp Ile Phe Arg Ala Ala Val Glu Leu Gly Tyr
    210                 215                 220

Arg Gly Ile Val Ile Glu Gly Tyr Gly Ala Gly Ile Pro Tyr Arg
225                 230                 235                 240

Gly Ser Asp Leu Leu Gln Thr Ile Glu Glu Leu Ser Lys Glu Ile Pro
                245                 250                 255

Ile Val Met Thr Thr Gln Ala Met Tyr Asp Gly Val Asp Leu Thr Arg
```

```
            260             265             270
Tyr Lys Val Gly Arg Leu Ala Leu Arg Ala Gly Val Ile Pro Ala Gly
            275             280             285

Asp Met Thr Lys Glu Ala Thr Val Thr Lys Leu Met Trp Ile Leu Gly
        290             295             300

His Thr Asn Asn Val Glu Glu Ile Lys Val Leu Met Arg Lys Asn Leu
305             310             315             320

Val Gly Glu Leu Arg Asp
            325

<210> SEQ ID NO 3
<211> LENGTH: 40
<212> TYPE: DNA
<213> ORGANISM: Artificial
<220> FEATURE:
<223> OTHER INFORMATION: chemically synthesized

<400> SEQUENCE: 3
acctgcggtc tcgcatgaaa attcttctaa ttgggatggg        40

<210> SEQ ID NO 4
<211> LENGTH: 36
<212> TYPE: DNA
<213> ORGANISM: Artificial
<220> FEATURE:
<223> OTHER INFORMATION: chemically synthesized

<400> SEQUENCE: 4
ggatccctgc agttaatctc taagctctcc aactag            36

<210> SEQ ID NO 5
<211> LENGTH: 3669
<212> TYPE: DNA
<213> ORGANISM: Artificial
<220> FEATURE:
<223> OTHER INFORMATION: plasmid pRSF-1b

<400> SEQUENCE: 5
tggtgtccgg gatctcgacg ctctccctta tgcgactcct gcattaggaa attaatacga      60
ctcactatag gggaattgtg agcggataac aattcccctg tagaaataat tttgtttaac     120
tttaataagg agatataccc atggcacatca ccaccaccat cacgtgggta ccggttcgaa     180
tgatgacgac gacaagagtc cggatcccaa ttgggagctc gtgtacacgg cgcgcctgca     240
ggtcgacaag cttgcggccg cactcgagtc tggtaaagaa accgctgctg cgaaatttga     300
acgccagcac atggactcgt ctactagcgc agcttaatta acctaggctg ctgccaccgc     360
tgagcaataa ctagcataac cccttggggc ctctaaacgg gtcttgaggg gttttttgct     420
gaaacctcag gcatttgaga agcacacggt cacactgctt ccggtagtca ataaaccggt     480
aaaccagcaa tagacataag cggctattta cgaccctgcc ctgaaccgac gacaagctg      540
acgaccgggt ctccgcaagt ggcactttc ggggaaatgt gcgcggaacc cctatttgtt     600
tatttttcta aatacattca aatatgtatc cgctcatgaa ttaattctta gaaaaactca     660
tcgagcatca aatgaaactg caatttattc atatcaggat tatcaatacc atattttga     720
aaaagccgtt tctgtaatga aggagaaaac tcaccgaggc agttccatag gatggcaaga     780
tcctggtatc ggtctgcgat tccgactcgt ccaacatcaa tacaacctat taatttcccc     840
tcgtcaaaaa taaggttatc aagtgagaaa tcaccatgag tgacgactga atccggtgag     900
aatggcaaaa gtttatgcat ttctttccag acttgttcaa caggccagcc attacgctcg     960
```

```
tcatcaaaat cactcgcatc aaccaaaccg ttattcattc gtgattgcgc ctgagcgaga    1020
cgaaatacgc ggtcgctgtt aaaaggacaa ttacaaacag gaatcgaatg caaccggcgc    1080
aggaacactg ccagcgcatc aacaatattt tcacctgaat caggatattc ttctaatacc    1140
tggaatgctg ttttcccggg gatcgcagtg gtgagtaacc atgcatcatc aggagtacgg    1200
ataaaatgct tgatggtcgg aagaggcata aattccgtca gccagtttag tctgaccatc    1260
tcatctgtaa catcattggc aacgctacct ttgccatgtt tcagaaacaa ctctggcgca    1320
tcgggcttcc catacaatcg atagattgtc gcacctgatt gcccgacatt atcgcgagcc    1380
catttatacc catataaatc agcatccatg ttggaattta atcgcggcct agagcaagac    1440
gtttcccgtt gaatatggct catactcttc cttttcaat attattgaag catttatcag    1500
ggttattgtc tcatgagcgg atacatattt gaatgtattt agaaaaataa acaaataggc    1560
atgcagcgct cttccgcttc ctcgctcact gactcgctac gctcggtcgt tcgactgcgg    1620
cgagcggtgt cagctcactc aaaagcggta atacggttat ccacagaatc aggggataaa    1680
gccggaaaga acatgtgagc aaaaagcaaa gcaccggaag aagccaacgc cgcaggcgtt    1740
tttccatagg ctccgccccc ctgacgagca tcacaaaaat cgacgctcaa gccagaggtg    1800
gcgaaacccg acaggactat aaagatacca ggcgtttccc cctggaagct ccctcgtgcg    1860
ctctcctgtt ccgaccctgc cgcttaccgg atacctgtcc gcctttctcc cttcgggaag    1920
cgtggcgctt tctcatagct cacgctgttg gtatctcagt tcggtgtagg tcgttcgctc    1980
caagctgggc tgtgtgcacg aaccccccgt tcagcccgac cgctgcgcct tatccggtaa    2040
ctatcgtctt gagtccaacc cggtaagaca cgacttatcg ccactggcag cagccattgg    2100
taactgattt agaggacttt gtcttgaagt tatgcacctg ttaaggctaa actgaaagaa    2160
cagattttgg tgagtgcggt cctccaaccc acttaccttg gttcaaagag ttggtagctc    2220
agcgaacctt gagaaaacca ccgttggtag cggtggtttt tctttattta tgagatgatg    2280
aatcaatcgg tctatcaagt caacgaacag ctattccgtt actctagatt tcagtgcaat    2340
ttatctcttc aaatgtagca cctgaagtca gccccatacg atataagttg taattctcat    2400
gttagtcatg ccccgcgccc accggaagga gctgactggg ttgaaggctc tcaagggcat    2460
cggtcgagat cccggtgcct aatgagtgag ctaacttaca ttaattgcgt tgcgctcact    2520
gcccgctttc cagtcgggaa acctgtcgtg ccagctgcat taatgaatcg ccaacgcgc    2580 ggggagaggc ggtttgcgta ttgggcgcca gggtggtttt tcttttcacc agtgagacgg    2640
gcaacagctg attgcccttc accgcctggc cctgagagag ttgcagcaag cggtccacgc    2700
tggtttgccc cagcaggcga aaatcctgtt tgatggtggt taacggcggg atataacatg    2760
agctgtcttc ggtatcgtcg tatcccacta ccgagatgtc cgcaccaacg cgcagcccgg    2820
actcggtaat ggcgcgcatt gcgcccagcg ccatctgatc gttggcaacc agcatcgcag    2880
tgggaacgat gccctcattc agcatttgca tggtttgttg aaaaccggac atggcactcc    2940
agtcgccttc ccgttccgct atcggctgaa tttgattgcg agtgagatat ttatgccagc    3000
cagccagacg cagacgcgcc gagacagaac ttaatgggcc cgctaacagc gcgatttgct    3060
ggtgacccaa tgcgaccaga tgctccacgc ccagtcgcgt accgtcttca tgggagaaaa    3120
taatactgtt gatgggtgtc tggtcagaga catcaagaaa taacgccgga acattagtgc    3180
aggcagcttc cacagcaatg gcatcctggt catccagcgg atagttaatg atcagcccac    3240
tgacgcgttg cgcgagaaga ttgtgcaccg ccgctttaca ggcttcgacg ccgcttcgtt    3300
```

```
ctaccatcga caccaccacg ctggcaccca gttgatcggc gcgagattta atcgccgcga    3360
caatttgcga cggcgcgtgc agggccagac tggaggtggc aacgccaatc agcaacgact    3420
gtttgcccgc cagttgttgt gccacgcggt tgggaatgta attcagctcc gccatcgccg    3480
cttccacttt ttcccgcgtt ttcgcagaaa cgtggctggc ctggttcacc acgcgggaaa    3540
cggtctgata agagacaccg gcatactctg cgacatcgta taacgttact ggtttcacat    3600
tcaccaccct gaattgactc tcttccgggc gctatcatgc cataccgcga aggttttgc     3660 gccattcga                                                            3669

<210> SEQ ID NO 6
<211> LENGTH: 4554
<212> TYPE: DNA
<213> ORGANISM: Artificial
<220> FEATURE:
<223> OTHER INFORMATION: Plasmid pRSF_PF-AsnI

<400> SEQUENCE: 6
tggtgtccgg gatctcgacg ctctccctta tgcgactcct gcattaggaa attaatacga      60
ctcactatag gggaattgtg agcggataac aattcccctg tagaaataat tttgtttaac     120
tttaataagg agatatacca tgaaaattct tctaattggg atgggtggaa caattgcgag     180
tgtaaagggc gagaatggat atgaggcttc gttgtccgtt aaagaagttt tagatatcgc     240
cggaatcaaa gattgtgagg attgtgattt ctcgattta aagaacgttg atagcacgct     300
tatccagcca gaagattggg tagatcttgc tgaaactctt tacaagaatg taaaaaaata     360
tgatggaatt atagtcactc atggtaccga tactcttgcc tacacttctt caatgataag     420
tttcatgctt agaaacccc caataccat cgtatttact ggttctatga tacctgccac      480
tgaagaaaat agtgatgccc ccctaaactt gcaaacagca ataaagtttg caacttctgg    540
aattagggga gtttacgtgg ccttcaatgg aaaagttatg cttggagtta aacatctaa     600 ggttaggaca atgagcagag atgcattcga aagcattaac taccctataa ttgcagaatt    660
aagaggagaa gatctcgtgg ttaactttat tccaaagttt aacaatggag aagtcacatt    720
agaccttagg cacgatccaa aagttctagt tataaagcta atcccaggac tttcggggga    780
catatttagg gcagctgtag agctgggata tagaggaatt gtcatagaag gttatggagc    840
tggaggaatt cctttataggg gaagtgattt acttcaaaca atagaggagc tctccaagga    900
gattccaata gtaatgacaa cccaggcaat gtacgatgga gttgatctaa cgaggtacaa    960
agttgggaga ttagccccta gagctggagt aatcccagcg ggggacatga caaaagaggc   1020
aacagtaaca aagctcatgt ggattctagg ccacacaaac aatgtggaag aaataaaagt   1080
attaatgaga aaaatctag ttggagagct tagagattaa ctgcaggtcg acaagcttgc    1140
ggccgcactc gagtctggta agaaaccgc tgctgcgaaa tttgaacgcc agcacatgga    1200
ctcgtctact agcgcagctt aattaaccta ggctgctgcc accgctgagc aataactagc   1260
ataacccctt ggggcctcta aacgggtctt gaggggtttt ttgctgaaac ctcaggcatt   1320
tgagaagcac acggtcacac tgcttccggt agtcaataaa ccggtaaacc agcaatagac   1380
ataagcggct atttaacgac cctgccctga accgacgaca agctgacgac cgggtctccg   1440
caagtggcac ttttcgggga atgtgcgcg gaacccctat ttgtttattt ttctaaatac    1500
attcaaatat gtatccgctc atgaattaat tcttagaaaa actcatcgag catcaaatga   1560
aactgcaatt tattcatatc aggattatca ataccatatt tttgaaaaag ccgtttctgt   1620
aatgaaggag aaaactcacc gaggcagttc cataggatgg caagatcctg gtatcggtct   1680
```

```
gcgattccga ctcgtccaac atcaatacaa cctattaatt tcccctcgtc aaaataagg   1740 ttatcaagtg agaaatcacc atgagtgacg actgaatccg gtgagaatgg caaaagttta   1800
tgcatttctt tccagacttg ttcaacaggc cagccattac gctcgtcatc aaaatcactc   1860
gcatcaacca aaccgttatt cattcgtgat tgcgcctgag cgagacgaaa tacgcggtcg   1920
ctgttaaaag gacaattaca aacaggaatc gaatgcaacc ggcgcaggaa cactgccagc   1980
gcatcaacaa tattttcacc tgaatcagga tattcttcta atacctggaa tgctgttttc   2040
ccggggatcg cagtggtgag taaccatgca tcatcaggag tacggataaa atgcttgatg   2100
gtcggaagag gcataaaatc cgtcagccag tttagtctga ccatctcatc tgtaacatca   2160
ttggcaacgc tacctttgcc atgtttcaga acaactctg gcgcatcggg cttcccatac    2220
aatcgataga ttgtcgcacc tgattgcccg acattatcgc gagcccattt atcccatat    2280 aaatcagcat ccatgttgga atttaatcgc ggcctagagc aagacgtttc ccgttgaata   2340
tggctcatac tcttcctttt tcaatattat tgaagcattt atcagggtta ttgtctcatg   2400
agcggataca tatttgaatg tatttagaaa aataaacaaa taggcatgca gcgctcttcc   2460
gcttcctcgc tcactgactc gctacgctcg gtcgttcgac tgcggcgagc ggtgtcagct   2520
cactcaaaag cggtaatacg gttatccaca gaatcagggg ataaagccgg aaagaacatg   2580
tgagcaaaaa gcaaagcacc ggaagaagcc aacgccgcag gcgttttcc ataggctccg    2640 cccccctgac gagcatcaca aaaatcgacg ctcaagccag aggtggcgaa acccgacagg   2700
actataaaga taccaggcgt ttccccctgg aagctccctc gtgcgctctc ctgttccgac   2760
cctgccgctt accggatacc tgtccgcctt tctcccttcg ggaagcgtgg cgctttctca   2820
tagctcacgc tgttggtatc tcagttcggt gtaggtcgtt cgctccaagc tgggctgtgt   2880
gcacgaaccc cccgttcagc ccgaccgctg cgccttatcc ggtaactatc gtcttgagtc   2940
caacccggta agacacgact tatcgccact ggcagcagcc attggtaact gatttagagg   3000
actttgtctt gaagttatgc acctgttaag gctaaactga agaacagat tttggtgagt     3060 gcggtcctcc aacccactta ccttggttca aagagttggt agctcagcga accttgagaa   3120
aaccaccgtt ggtagcggtg gttttctttt atttatgaga tgatgaatca atcggtctat   3180
caagtcaacg aacagctatt ccgttactct agatttcagt gcaatttatc tcttcaaatg   3240
tagcacctga agtcagcccc atacgatata agttgtaatt ctcatgttag tcatgccccg   3300
cgcccaccgg aaggagctga ctgggttgaa ggctctcaag ggcatcggtc gagatcccgg   3360
tgcctaatga gtgagctaac ttacattaat tgcgttgcgc tcactgcccg ctttccagtc   3420
gggaaacctg tcgtgccagc tgcattaatg aatcggccaa cgcgcgggga gaggcggttt   3480
gcgtattggg cgccagggtg ttttctttt tcaccagtga cgggcaac agctgattgc      3540 ccttcaccgc ctggccctga gagagttgca gcaagcggtc cacgctggtt tgccccagca   3600
ggcgaaaatc ctgtttgatg gtggttaacg gcgggatata acatgagctg tcttcggtat   3660
cgtcgtatcc cactaccgag atgtccgcac caacgcgcag cccggactcg gtaatggcgc   3720
gcattgcgcc cagcgccatc tgatcgttgg caaccagcat cgcagtggga acgatgccct   3780
cattcagcat ttgcatggtt tgttgaaaac cggacatggc actccagtcg ccttcccgtt   3840
ccgctatcgg ctgaatttga ttgcgagtga tatttatg ccagccagcc agacgcagac     3900
gcgccgagac agaacttaat gggcccgcta acagcgcgat ttgctggtga cccaatgcga   3960
ccagatgctc cacgcccagt cgcgtaccgt cttcatggga gaaaataata ctgttgatgg   4020
```

```
gtgtctggtc agagacatca agaaataacg ccggaacatt agtgcaggca gcttccacag    4080
caatggcatc ctggtcatcc agcggatagt taatgatcag cccactgacg cgttgcgcga    4140
gaagattgtg caccgccgct ttacaggctt cgacgccgct tcgttctacc atcgacacca    4200
ccacgctggc acccagttga tcggcgcgag atttaatcgc cgcgacaatt tgcgacggcg    4260
cgtgcagggc cagactggag gtggcaacgc caatcagcaa cgactgtttg cccgccagtt    4320
gttgtgccac gcggttggga atgtaattca gctccgccat cgccgcttcc acttttcccc    4380
gcgttttcgc agaaacgtgg ctggcctggt tcaccacgcg ggaaacggtc tgataagaga    4440
caccggcata ctctgcgaca tcgtataacg ttactggttt cacattcacc accctgaatt    4500
gactctcttc cgggcgctat catgccatac cgcgaaaggt tttgcgccat tcga          4554
```